United States Patent [19]

Solomon et al.

[11] 4,086,228
[45] Apr. 25, 1978

[54] PROCESS FOR PREPARING CYCLOTETRAMETHYLENETETRANITRA-MINE

[75] Inventors: Irvine J. Solomon, Chicago, Ill.; Louis B. Silberman, Dover, N.J.

[73] Assignee: The United States of America as represented by the Secretary of the Army, Washington, D.C.

[21] Appl. No.: 734,685

[22] Filed: Oct. 22, 1976

[51] Int. Cl.$^2$ ............................................. C07D 257/02
[52] U.S. Cl. ............................................. 260/239 HM
[58] Field of Search ............................... 260/239 HM

[56] References Cited

U.S. PATENT DOCUMENTS

| | | | |
|---|---|---|---|
| 2,434,879 | 1/1948 | Wright et al. | 260/248 NS |
| 2,525,252 | 10/1950 | Willson et al. | 260/248 NS |
| 3,093,640 | 6/1963 | Hull | 260/248 NS |
| 3,770,721 | 11/1973 | Robbins et al. | 260/239 HM |

Primary Examiner—Donald G. Daus
Assistant Examiner—D. B. Springer
Attorney, Agent, or Firm—Nathan Edelberg; A. Victor Erkkila; Harold H. Card, Jr.

[57] ABSTRACT

HMX is obtained in substantially increased amount by means of a novel modification of the conventional process for producing HMX by reaction of hexamine with a nitrating agent consisting of $HNO_3$—$NH_4NO_3$ solution in acetic acid-acetic anhydride medium, wherein the nitrating agent, hexamine solution and acetic anhydride are concurrently added to a mixture of acetic acid and acetic anhydride called a "heel". The modification involves incorporating a small amount of hexamine in the heel prior to the addition of a major portion of the nitrating agent.

7 Claims, No Drawings

PROCESS FOR PREPARING CYCLOTETRAMETHYLENETETRANITRAMINE

GOVERNMENT INTEREST

The invention described herein was made in the course of a contract with the U.S. Government.

BACKGROUND OF THE INVENTION

The present invention relates to an improvement in the process for preparing cyclotetramethylenetetranitramine, commonly and hereinafter referred to as HMX.

HMX is a powerful explosive of considerable military interest. The batch process currently practiced for the manufacture of HMX is a variation of the original Bachmann process consisting of the nitrolysis of hexamethylenetetramine, usually and hereinafter referred to as hexamine, with a mixture of nitric acid and ammonium nitrate in a medium of acetic acid and acetic anhydride. The batch nitration process is commonly divided into four parts or stages: a first addition of reagents followed by a first aging period; then a second addition of reagents followed by a second aging period. More specifically, the process is carried out by charging the reaction vessel with a mixture or "heel" of acetic acid and acetic anhydride to provide a stirrable liquid medium into which the reagents are introduced. The first addition of reagents is then made by concurrently and proportionately introducing separate streams of a solution of hexamine in glacial acetic acid, a solution of ammonium nitrate in conc. nitric acid, and acetic anhydride, after which the reaction mixture is agitated and permitted to age for several minutes. Thereafter, a second addition of reagents is made by concurrently and proportionately introducing separate streams of acetic anhydride and a solution of ammonium nitrate in conc. nitric acid, after which the reaction mixture is agitated and allowed to age for a substantial period. During these operations the temperature of the reaction mixture is usually maintained at about 40°–45° C. Following the second aging period the reaction mixture is diluted with water, which hydrolyzes any excess acetic anhydride and dilutes the acetic acid concentration to about 80 weight percent. The mixture is then heated to about 110° C. to decompose undesirable by-products, such as linear nitramines, and then filtered to isolate the HMX product.

SUMMARY AND DESCRIPTION OF THE INVENTION

A principal object of the invention is to provide an improvement in the conventional batch process for producing HMX, whereby a substantially greater amount of HMX can be obtained in a simple and economical manner. Other objects will become apparent as the invention is further described.

In accordance with this invention the foregoing objects are accomplished by a novel modification of the conventional batch process for HMX, which comprises incorporating a small amount of hexamine in the heel of acetic acid acetic anhydride prior to the addition of a major portion of the nitrating agent $HNO_3$—$NH_4NO_3$.

The following examples illustrate specific embodiments of the method of carrying out the process of the present invention.

EXAMPLE 1

The reactor vessel was a 1000 ml. flask fitted with a cover containing four ground glass connections and a mechanical stirrer. The reactor vessel was surrounded by a temperature-controlled water bath and contained a stainless steel cooling coil for cooling the reaction mixture. The acetic acid, acetic anhydride and the $HNO_3$—$NH_4NO_3$ solution were introduced through three of the ground glass connections, while cooling or heating water, as required, was circulated through the cooling coil via the fourth glass connection.

50.6 grams of glacial acetic acid, 4.1 grams of acetic anhydride and 4.0 grams of hexamine were charged to the reactor vessel to serve as a heel. An analysis of the heel showed that it contained excess acetic anhydride at this point. The temperature of the reactor contents was then raised to 43° C. and maintained thereat during the remainder of the run.

The first addition of the reagents was made by introducing into the reactor vessel continuously and proportionately during 21 minutes 53.4 grams of a 38% hexamine solution consisting of 20.3 grams of hexamine and 33.1 grams of glacial acetic acid, 33.2 grams of a 56.4% $HNO_3$—$NH_4NO_3$ solution consisting of 18.7 grams of $HNO_3$ and 14.5 grams of $NH_4NO_3$, and 105.7 grams of acetic anhydride. The reaction mixture was then aged for 6 minutes before the second addition of reagents was made.

The second addition was performed in two parts: Part 1 consisted of adding 10.5 grams of a 56.4% $HNO_3$—$NH_4NO_3$ solution consisting of 5.9 grams of $HNO_3$ and 4.6 grams of $NH_4NO_3$, and 34.1 grams of acetic anhydride to the reactor vessel continuously and proportionately during 7 minutes; Part 2 following Part 1 consisted of adding 41.3 grams of the 56.4% $HNO_3$—$NH_4NO_3$ solution consisting of 23.3 grams of $HNO_3$ and 18.0 grams of $NH_4NO_3$, and 129.1 grams of acetic anhydride to the reactor vessel continuously and proportionately over a period of 8 minutes.

When the second addition was complete, the reaction mixture was aged for 30 minutes. Thereafter the reaction mixture was transferred to another vessel and mixed with sufficient dilute aqueous acetic acid to hydrolyze any excess acetic anhydride and reduce the concentration of the mixture to 80 weight percent acetic acid. The diluted reaction mixture was heated at 110° C. for one hour to effect the usual simmering operation to eliminate by-products, notably linear nitramines formed during the reaction, then cooled to 30° C. and filtered to separate the HMX product, which was washed with cold water and dried.

The following table sets forth the results obtained in the foregoing example and other examples conducted in identical manner except that different amounts of hexamine were added to the heel, as compared with the result obtained in the same standard manner when no hexamine was added to the heel Table

| Example No. | Hexamine Added to Heel | Yield* % Crude HMX | Purity % HMX | Yield* % HMX | HMX Formed, Grams |
|---|---|---|---|---|---|
| 1 | 4 | 95.4/79.5 | 84.3 | 80.4/67.0 | 34.5 |
| 2 | 4 | 97.4/81.5 | 84.8 | 82.6/69.1 | 35.3 |
| 3 | 2 | 86.2/78.4 | 86.7 | 74.7/68.0 | 32.0 |

Table-continued

| Example No. | Hexamine Added to Heel | Yield* % Crude HMX | Purity % HMX | Yield* % HMX | HMX Formed, Grams |
|---|---|---|---|---|---|
| 4 | 6 | 99.0/76.6 | 81.2 | 80.4/62.2 | 34.5 |
| 5 | 0 | 76.3 | 88.2 | 67.3 | 28.4 |

*The first figure indicated the yield based hexamine excluding hexamine present in the heel; the second figure represents the yield based on total hexamine added including hexamine present in the heel. The impurities in the crude HMX consist mainly of RDX.

From the table it is evident that by means of the present invention the amount of HMX produced per batch can be increased by up to 24% (from 28.4% (from 28.4 grams to 35.3 grams). Since the cost of hexamine is about 10% that of HMX, the simple modification of the standard process according to the present invention can provide substantial economies.

The substantially increased amount of HMX obtained according to the present invention is unexpected and not understood, since it is not obtained when the experiment described above is repeated except that instead of adding the aforementioned amount of hexamine to the heel, the same amount of hexamine is incorporated in the hexamine solution introduced with the nitrating agent during the experiment.

An increased yield of HMX can also be obtained according to the process of the present invention even if the addition of the hexamine to the heel is made after a portion — but not a major portion — of the HNO$_3$.—NH$_4$NO$_3$ nitrating agent and all of the hexamine solution have been added to said heel of acetic acid and acetic anhydride. Thus, when the procedure of example 1 was repeated except that instead of adding 4 grams of hexamine to the heel prior to the first addition of the reagents thereto, 2.6 grams of hexamine were added to the heel at the end of the first addition of the reagents and before the first age period, the amount of HMX obtained, based on hexamine introduced but excluding hexamine added to the heel, was 17% higher than that obtained in standard manner when no hexamine was added to the heel.

Further, the total amounts of the reagents employed in the process can be added concurrently to the heel without the necessity of any intermediate age period when the hexamine additive is incorporated in the heel prior to addition of the reagents thereto. Thus, the amount of HMX produced (based on hexamine feed but not including hexamine added to the heel) was 14% higher than that obtained in standard manner when the procedure of example 1 was repeated with the exception that 2.6 grams instead of 4 grams of hexamine were added to the heel and the age period between the first and second additions of the reagents was eliminated.

In carrying out the preparation of HMX according to the process of the present invention the nitric acid, ammonium nitrate and acetic anhydride employed are preferably used in amounts of from about 5–7 moles of HNO$_3$, from about 3–5 moles of NH$_4$NO$_3$ and from about 12–20 moles of acetic anhydride per mole of hexamine, excluding the amount of hexamine additive incorporated in the heel. In the reactions described in the foregoing examples, the reagents were employed in the molar ratios of 5.2 moles HNO$_3$, 3.2 mols NH$_4$NO$_3$ and 18.5 moles acetic anhydride per mole of hexamine, not including hexamine additive in the heel. As shown in the examples, the additional amount of HMX produced by incorporating hexamine additive in the heel reaches a maximum when about 4 grams of hexamine additive is employed, corresponding to about 0.2 mole per mole of hexamine introduced with the reagents in standard manner. Further amounts of hexamine additive to the heel provide little, if any, additional increase in the amount of HMX produced and hence provide little, if any, additional economic advantage. The hexamine additive is advantageously employed in an amount between about 0.05 and 0.5 mole, and preferably between about 0.1 and 0.3 mole, per mole of hexamine introduced with the other reactants. The reaction is preferably carried out at a temperature between about 40° and 45° C.

The heel of acetic acid and acetic anhydride is conventionally employed to provide a readily stirrable medium into which the reagents are introduced. According to the present process the hexamine additive is preferably incorporated in the heel before addition of the reagents thereto; but it can be incorporated even after all of the hexamine solution but before a major portion of the nitrating agent have been introduced. After the incorporation of the hexamine additive, the heel preferably contains free acetic anhydride and is agitated for a period prior to introduction of the reactants.

The foregoing disclosure is merely illustrative of the principles of this invention and is not to be interpreted in a limiting sense. We wish it to be understood that we do not desire to be limited to the exact details of construction shown and described, because obvious modifications will occur to a person skilled in the art.

What is claimed is:
1. In the process of preparing cyclotetramethylenetetranitramine, which comprises reacting hexamine in an acetic acid-acetic anhydride medium with nitric acid-ammonium nitrate nitrating agent in two stages at a temperature between about 40° C and 45° C, characterized in the first reaction stage by the addition of all the hexamine and a minor amount of the nitrating agent and acetic anhydride to a heel consisting essentially of acetic acid-acetic anhydride mixture followed by an optional aging period, and in the second reaction stage by the addition of the remaining, major amount of the nitrating agent and acetic anhydride followed by an aging period, the improvement which comprises the step of incorporating therein
   (a) before the addition of said reactants in said first reaction stage, or
   (b) after the addition of said reactants in said first reaction stage but before the aging period in said first reaction stage a minor amount up to 0.5 mole of hexamine per mole of hexamine introduced with said nitrating agent.
2. The process of claim 1, wherein the nitric acid is employed in the ratio of from about 5 to 7 moles per mole of hexamine, the ammonium nitrate is employed in the ratio of from about 3 to 5 moles per mole of hexamine, and the acetic anhydride is employed in the ratio of from about 12 to 20 moles per mole of hexamine.
3. The process of claim 2, wherein the minor amount of hexamine incorporated in the heel amounts to between about 0.1 and 0.3 mole per mole of hexamine introduced with the nitrating agent.

4. The process of claim 2, wherein said minor amount of hexamine is incorporated after the addition of the hexamine, nitrating agent and acetic anhydride in the first reaction stage but before the aging period in said first reaction stage.

5. The process of claim 2, wherein said minor amount of hexamine is incorporated in the heel before said first reaction stage.

6. The process of claim 5, wherein about 1 mol of hexamine, 2.1 mols of nitric acid, 1.6 mols of ammonium nitrate and 7 mols of acetic anhydride are introduced in the first stage, and about 3.2 mols of nitric acid, 2.4 mols of ammonium nitrate and 11 mols of acetic anhydride are introduced in the second reaction stage.

7. The process of claim 5, wherein the aging period is omitted in said first stage.

* * * * *